United States Patent [19]
Choulet et al.

[11] 4,271,316
[45] Jun. 2, 1981

[54] PROCESS FOR THE CONTINUOUS REARRANGEMENT OF ALKALI METAL SALTS OF AROMATIC CARBOXYLIC ACIDS

[75] Inventors: Jean-Claude Choulet, Meyzieu; Jacques Nouvel, Tassin la Demi-Lune, both of France

[73] Assignee: Rhone-Poulenc Industries, Paris, France

[21] Appl. No.: 59,383

[22] Filed: Jul. 20, 1979

Related U.S. Application Data

[63] Continuation of Ser. No. 858,274, Dec. 7, 1977, abandoned.

[30] Foreign Application Priority Data

Dec. 9, 1976 [FR] France ............................... 76 37838

[51] Int. Cl.³ .................. C07C 51/347; C07C 51/353
[52] U.S. Cl. .................................... 562/480; 562/479; 562/481
[58] Field of Search ...................... 562/481, 482, 479

[56] References Cited

U.S. PATENT DOCUMENTS 3,781,341 12/1973 Wu et al. ............................. 562/481
3,873,609 3/1975 Wu et al. ............................. 562/481

FOREIGN PATENT DOCUMENTS 39-10331 6/1964 Japan ...................................... 562/482
990611 4/1965 United Kingdom ..................... 562/482

Primary Examiner—Jane S. Myers
Attorney, Agent, or Firm—Burns, Doane, Swecker & Mathis

[57] ABSTRACT

A process for the continuous rearrangement of alkali metal salts of aromatic carboxylic acids is disclosed. The process is conducted under an atmosphere of carbon dioxide and in the presence of an organic diluent and results in high conversion rates and practically quantitative yields of the rearranged alkali metal salt of the aromatic carboxylic acid.

17 Claims, No Drawings

PROCESS FOR THE CONTINUOUS REARRANGEMENT OF ALKALI METAL SALTS OF AROMATIC CARBOXYLIC ACIDS

This is a continuation of application Ser. No. 858,274, filed Dec. 7, 1977, now abandoned.

BACKGROUND OF THE INVENTION

1. Field of the Invention

The present invention is directed to a process for the continuous arrangement of alkali metal salts of aromatic carboxylic acids in the presence of an organic diluent. In particular, it concerns a process for the dismutation of potassium benzoate.

2. Description of the Prior Art

High temperature rearrangement of the alkali metal salts of aromatic carboxylic acids into different salts of aromatic carboxylic acids having at least two carboxyl groups in the molecule is well documented in technical literature. The rearrangement reaction can be a dismutation reaction, producing an aromatic polycarboxylate containing at least one additional carboxyl group. Additionally, the rearrangement reaction can be an isomerization reaction, during which the number of the carboxyl groups attached to the same molecule remains unchanged, but in which the position of these various groups changes.

The method of rearranging alkali metal salts of aromatic mono-or polycarboxylic acids, commonly referred to as the Henkel process, was first performed by heating the salts in the solid state in the presence of a protective gas such as nitrogen or carbon dioxide. Unfortunately, this reaction in the solid or partially molten state causes tremendous technical difficulties when performed on the industrial scale. These difficulties arise from the low heat transfer in the reactor as well as the problems associated with transportation and mixing of both the reactants and the reaction products. Moreover, the solids have a tendency to agglomerate and form dross, which increases handling difficulty.

Consequently, it was proposed to perform the rearrangement reaction so that an inert diluent is used to transport the solids in the form of a suspension. This technique was described in French Pat. No. 1,105,556 and British Pat. No. 810,893. In these cases the processes were performed discontinuously and the recommended diluent was benzene or naphthalene, biphenyl, diphenylether, or pyridine.

The rearrangement method for alkali metal salts of aromatic carboxylic acids employing suspensions in an inert diluent was subsequently improved by the selection of more suitable diluents. Thus, it was recommended in French Pat. No. 2,143,401 to use as the diluent, aromatic hydrocarbons having at least three aromatic rings such as the aromatic polynucleic products. Examples of these dispersion products are the terphenyls, tetraphenyls, pentaphenyls, binaphytyls, anthracene, phenanthrene, pyrene, triphenylene, chrysene, perylene, and pentacene. As set forth in French Pat. No. 2,143,401, the use of these diluents permits one to perform the rearrangement reaction at very high conversion rates, resulting in a higher yield of the final product. Although the process described by the patent is performed discontinuously, there is an indication, without a description, that a continuous operation could be performed in a manner such that the suspension of the alkali metal salts of the aromatic carboxylic acids are moved by pumps. The possibility of performing the rearrangement reaction continuously is also suggested and generally described in French Pat. No. 2,213,266.

Unfortunately, the continuous rearrangement processes performed in the presence of a diluent as described in the prior art give much poorer results than those provided by discontinuous operations. In particular, for the same conversion rate, the yields of the continuous operation are much lower than those of the discontinuous operation. Thus, there remains a need in the art for a continuous process for rearranging alkali metal salts of aromatic carboxylic acids which provides yields as high as the discontinuous processes known to those of skill in the art.

SUMMARY OF THE INVENTION

Accordingly, it is a primary object of the present invention to provide a continuous process for the rearrangement of alkali metal salts of aromatic carboxylic acids in the presence of an inert liquid organic diluent which results in high conversion rates and practically quantitative yields of the alkali metal salts of the aromatic carboxylic acids.

Another object of the invention is to provide an improved method for continuously preparing rearranged aromatic carboxylic acids from alkali metal salts of aromatic carboxylic acids.

Still another object of the invention is the production of terephthalic acid in high yields from potassium benzoate.

Other objects and advantages of the invention will be evident to those of skill in the art upon studying the detailed description which follows.

DETAILED DESCRIPTION OF THE INVENTION

The foregoing objects and advantages of the invention are accomplished by providing a process for the continuous rearrangement of alkali metal salts of aromatic carboxylic acids under an atmosphere of carbon dioxide in a liquid reaction medium containing an inert organic diluent. The alkali metal salts are continuously introduced, in the form of a suspension, into the diluent in a reaction circuit comprising a feeding device including means for preheating the suspension. Carbon dioxide is continuously introduced into the reactor via the feeding circuit in combination with the suspension of alkali metal salts of the aromatic carboxylic acid. The introduction of the carbon dioxide is performed at any place in the feeding circuit where the temperature is below that required to effect the rearrangement reaction.

In the context of the present invention, the term rearrangement reaction is meant to connote both an isomerization and a dismutation reaction. In the isomerization reaction, the number of carboxyl groups in the reactant and product is the same, but their position on the product molecule is different. The dismutation reaction produces an aromatic polycarboxylate containing at least one additional carboxyl group than the reactant molecule.

The partial pressure of carbon dioxide in the reaction zone generally ranges from about 20 to 400 bars and preferably from about 30 to 200 bars. Increasing the partial pressure of carbon dioxide in the reaction zone advantageously results in an increase in the rate of conversion of the alkali metal salt of the aromatic carboxylic acid for a given reaction temperature and retention time. However, the partial pressure of carbon dioxide should not be increased excessively as this results in added technological difficulties on an industrial scale. Additionally, high carbon dioxide pressures initiate various secondary reactions, which interfere with the rearrangement reaction.

A characteristic feature of the process of the present invention is the continuous introduction of carbon dioxide through the feeding circuit in the suspension of the alkali metal salt of the aromatic carboxylic acid. The feeding circuit comprises a feeding pump of any known type and a conventional preheating system for heating the suspension of the alkali metal salt of the aromatic carboxylic acid. The preheating system must be capable of heating the suspension of the alkali metal salt to a temperature of about 350° to 500° C. and preferably about 430° to 480° C.

The carbon dioxide is continuously admitted into the feeding system of the suspension of any place in the system where the temperature of the suspension is lower than that required to initiate the rearrangement of the alkali metal salt higher than the melting point of the organic diluent. Generally, the carbon dioxide is introduced at any place in the feeding circuit where the temperature is between about 70° and 350° C. According to a preferred embodiment, the carbon dioxide is introduced into the circuit prior to the preheating device. The carbon dioxide may, optionally, be preheated to temperatures in the range of 150° C. prior to introduction into the feeding circuit.

The amount of carbon dioxide introduced into the system is such that the yield of rearranged products is practically 100%. For this purpose, a partial pressure of carbon dioxide exceeding about 20 bars, and preferably exceeding about 30 bars, in both the feeding circuit and the reaction zone is generally sufficient. Thus, for example, using the continuous process of the present invention one can dismute potassium benzoate at a temperature between about 430° and 480° C., under a partial pressure of carbon dioxide between about 30 and 200 bars and still obtain conversion rates in the order of 70 to 90% with practically 100% yield of dipotassium phthalate.

It is understood that the process of the present invention is not limited to the use of pure carbon dioxide. In fact, mixtures of carbon dioxide with other gases such as nitrogen, carbon monoxide and methane are equally effective. However, the partial pressure of the carbon dioxide in the system must always be at least equal to about 20 bars.

The carbon dioxide introduced into the feeding circuit may be obtained, in whole or in part, by recycling the carbon dioxide recovered at the outlet of the reaction zone after separating the condensable products and effecting the final purge. The volume of the carbon dioxide in the system is controlled so that there is a constant partial pressure of carbon dioxide in the reaction zone. It is possible to introduce the carbon dioxide into the feeding system by way of the suspension of the alkali metal salt of the aromatic carboxylic acid as well as directly into the reaction zone.

The process of the present invention is especially adapted for the rearrangement of an alkali metal benzoate, particularly potassium benzoate. The latter can be used pure or with low amounts of alkali metal phthalates. This mixture is of particular industrial interest as it is obtained during the precipitation of terephthalic acid after addition of benzoic acid to an aqueous solution of dipotassium terephthalate. However, the process is equally effective in rearranging alkali metal salts of other aromatic mono- or polynuclear, mono- or polycarboxylic acids. These compounds may be represented generally by the following formula:

$$R\text{---}(COOH)_n$$

wherein R represents a hydrocarbon radical having from 6 to 15 carbon atoms selected from the group consisting of mono- and polynuclear aromatic groups having at most three benzene rings, and mono- and polynuclear alkylaromatic groups having at most three benzene rings, and n is an integer equal to 1, 2 or 3. Exemplary of these acids are o-phthalic and isophthalic acids, biphenyl acids, mono- and dicarboxylic biphenyl acids, carboxylic-2 naphthalene acid, dicarboxylic-2,6 naphthalene acid, carboxylic-2 anthracene acid, dicarboxylic-2,5 anthracene acid, tricarboxylic 2,3,4 anthracene acid, carboxylic-3 phenanthrene acid, and trimethyl 2,3,4 benzene carboxylic acid. In all these carboxylic acid salts the aromatic ring may include alkyl radicals in addition to the carboxylate groups, provided they do not cause decomposition of the molecule during the rearrangement reaction.

The diluent used in the process of the invention is an organic compound having a high boiling point, which is liquid and chemically inert under the reaction conditions. By chemically inert is meant inert under the general reaction conditions. However, as the temperature or pressure of $CO_2$ is increased to the contemplated upper limits, slight changes in the inertness can be expected and will not seriously effect the rearrangement reaction.

The diluents which are useful in the present invention are well known to those of skill in the art. Such diluents are described in the British Pat. No. 810,893 and in the French Pat. Nos. 1,105,556 and 2,143,401. Generally, diluents with comparatively high boiling points such as aromatic hydrocarbons having at least 3 benzene rings, in particular the terphenyls and the tetraphenyls optionally containing the higher polyphenyls are well suited for the practice of the invention. Mixtures of ortho-, meta- and para terphenyl, containing less than 6% of p-terphenyl and less than 60% of higher polyphenyls having at least four benzene rings in their molecule, are very attractive diluents, due to their low boiling point which falls between about 50° and 100° C. Preferably, mixtures of terphenyls, containing at most 5% of p-terphenyl and possibly up to 30% of higher polyphenyls, are used.

The diluent is commonly present in the suspension of the alkali metal salt of the aromatic carboxylic acid in amounts ranging from about 40 to 90% based on total mass of the suspension and preferably from about 60 to 80%. Although the suspension is preferably anhydrous, it may contain low amounts of water, generally up to about 800 ppm without adversely affecting the reaction. The permissive inclusion of low amounts of water is quite surprising since known methods have considered the inclusion of water harmful as fostering adverse secondary reactions.

The reaction can be performed with or without the presence of a catalyst. Suitable catalysts are oxide salts of mineral or organic acids and organo-metallic complexes of metals such as zinc, cadmium, mercury, lead, or iron. Of these latter compounds the following are exemplary: carbonates, bicarbonates, halides, sulfates, formiates, phosphates and salts of fatty acids. The preferred catalysts are based on zinc and cadmium and include: cadmium oxide, cadmium iodide, cadmium chloride, cadmium benzoate, metallic zinc, zinc oxide, zinc iodide, zinc chloride, zinc sulfate, zinc acetate, zinc benzoate, zinc isophthalate, zinc orthophthalate, and zinc terephthalate.

The amount of the catalyst employed varies within wide limits, generally ranging from about 0.1 to 40 g of catalyst per mole of aromatic carboxylate used. Preferably, the amount ranges from about 1.5 to 5 g of catalyst per mole of carboxylate. The catalyst is generally present in a finely divided state and may be deposited on inert supports such as kieselguhr or carbon.

The conversion of the alkali metal carboxylate conducted at temperatures between about 350° and 500° C. and preferably between about 430° and 480° C., under an oxygen-free atmosphere comprised on carbon dioxide. The reaction zone generally comprises a reactor capable of withstanding the conditions of the reaction. Since the type of reactor is not critical, any conventional reactor type may be used to carry out the rearrangement reaction. It is, thus, conceivable to employ a lone reactor or a cascade of reactors which are preferably agitated, as the reaction zone. Other equally operable reactors include a piston-type reactor or a countercurrent column in which the carbon dioxide circulates from bottom to top.

The catalyst is introduced continuously into the reactor as either a suspension or solution with an inert organic diluent. Preferably, the catalyst suspension is introduced directly into the reactor via a feed which is separate from the carboxylate feed. The catalyst suspension can be preheated, possibly under an atmosphere of carbon dioxide prior to introduction into the reactor. According to a variation of the process, the catalyst suspension is introduced into the reactor via the feeding circuit for the suspension of the alkali metal salt of the aromatic carboxylic acid which is also preheated under an atmosphere of carbon dioxide prior to introduction into the reactor.

The rearrangement reaction can also be performed in the presence of potassium salts of cyanic acid derivatives or polymers thereof. Examples of these compounds are: cyanuric acid, cyanamide and dicyanodiamide. These additives benefit the rearrangement reaction as described in French Pat. No. 2,143,401.

The alkali metal aromatic acid salts prepared according to the process of the invention are recovered from the reaction medium by any known means. For example, the diluent can be separated by extraction with an aromatic solvent, i.e., benzene, toluene and analogs thereof, or evaporation or sublimation at the outlet of the reaction zone. The solid salts are subsequently purified and transformed into carboxylic acids by any known means. Additionally, the alkali metal salts of the aromatic carboxylic acids can be recovered from the suspension that exits the reactor by addition of water, separation of the catalyst, and subsequent decantation. The resulting aqueous solution which contains the product alkali metal salts is then purified to remove the solvent and coloration, and is finally treated with an acid, such as the benzoic acid, to obtain the aromatic acid in a free state.

The products obtained by the rearrangement process of the present invention for a given aromatic carboxylic acid salt reactant are known to those of skill in the art and described in literature, as for example, U.S. Pat. No. 3,787,487. Generally, the alkali metal salts of aromatic monocarboxylic acids are dismutated into an aromatic hydrocarbon and an aromatic dicarboxylic acid salt. For instance, when a benzoate is the reactant, benzene and terephthalate are formed by the rearrangement process. On the other hand, the alkali metal salts of aromatic dicarboxylic acids are isomerized into other dicarboxylic acid salts by the present invention. Thus, when the reactant salt is orthophthalate or isophthalate, terephthalate is the isomer product. Finally, the salts of aromatic tricarboxylic acids can be rearranged, in the presence of the salts of the monocarboxylic acid, producing aromatic dicarboxylic acid salts.

The rearranged aromatic carboxylic acid salts prepared according to the invention may be converted to their respective aromatic carboxylic acids by addition of an acid, such as hydrochloric acid. Thus, for example, when potassium benzoate is rearranged by the present process to form dipotassium terephthalate which is subsequently treated with hydrochloric acid, terephthalic acid is produced in extremely high yields.

The process according to the invention is of great industrial interest in the production of fibrous grade terephthalic acid through the continuous dismutation of potassium benzoate at a higher rate of conversion than heretofore known and with practically quantitative yields. Other advantages of the process include: the lower content of catalyst and the ability to use a suspension of alkali metal salts of aromatic carboxylic acid, containing very low amounts of water.

The following examples are provided to further illustrate the present invention. It is understood that their purpose is entirely illustrative and in no way intended to limit the scope of the invention.

EXAMPLE 1

A suspension of potassium benzoate, 30% by weight/weight was introduced into a continuously operated, agitated reactor maintained at 450° C. in an isomeric mixture of terphenyls (composition: p-terphenyl 5%; o-terphenyl 25%, m-terphenyl 70%) at the rate of 1.2 kg/h. The feeding circuit of the suspension consisted of a feeding pump and preheating device. Carbon dioxide at 200° C. was also introduced into the feeding pipeline of the potassium benzoate suspension between the pump and the preheater. The admission was controlled by a valve set so that the partial pressure of $CO_2$ was continuously 40 bars at the valve outlet. At the outlet of the preheating unit the temperature of the potassium benzoate suspension was 460° C.

A suspension of zinc benzoate in the same isomeric mixture of terphenyls (concentration 20% by weight/weight) was introduced at the rate of 0.043 kg/hr via a second circuit comprising a feeding pump and a preheating device. Carbon dioxide at 200° C. was also introduced between the pump and the preheater under a partial pressure of 40 bars. The catalyst suspension was preheated to 300° C. before its introduction into the reactor.

A suspension of dipotassium phthalates in terphenyls was released from the reactor at a rate of 1.1 kg/hr. The gases were evacuated at the top of the reactor so that a constant pressure of 50 bars was maintained in the reactor. The gases were collected, cooled to 100° C. and reused as the source of carbon dioxide after purging.

The dipotassium phthalate suspension was diluted with water. The carbon residues were separated by filtration and the water layer was decanted. The latter was extracted with toluene and treated with black. Terephthalic acid was precipitated from the water layer upon addition of hydrochloric acid. The terephthalic acid was obtained at a rate of 126.5 g/hr. By metering the mother liquor the hourly production of orthophthalate was determined to be 9.5 g. No isophthalate was formed. The rate of conversion of the potassium benzoate was 73% and the yields of orthophthalate and terephthalate were 7 and 92.8%, respectively.

For the purpose of comparison the procedure of Example 1 was identically followed, with the reactants being heated to 430° C. However, the carbon dioxide was not introduced into either feeding circuit. Rather, it was introduced directly into the reactor. All other conditions were the same as in Example 1. The rate of conversion of potassium benzoate was 88% and the yield of the phthalates with respect to the converted potassium benzoate was 85%.

EXAMPLE 2

The same apparatus as that described in Example 1 was used. A potassium benzoate suspension was introduced in the terphenyls at the rate of 1.2 kg/hr and a suspension of zinc benzoate was introduced into the terphenyls at the rate of 0.040 kg/hr. The suspensions were identical to those used in Example 1. The carbon dioxide was transported in the two feeds in such a manner that the partial pressure of the carbon dioxide in the reactor was maintained at 150 bars, the temperature in the reactor being 470° C.

The observed rate of conversion of potassium benzoate was 89% and the yield of phthalates with respect to the converted potassium benzoate was 99%.

EXAMPLE 3

In this test, a suspension containing both the potassium benzoate and the zinc benzoate was introduced into a piston reactor. The feeding circuit additionally comprised a preheater and a pipe by which the partial pressure of the carbon dioxide was maintained constant at 40 bars. The carbon dioxide was introduced into the circuit between the feeding pump and the preheater.

Operating at temperatures and total volumes that were identical to those used in Example 1, the rate of conversion of potassium benzoate was observed to be 76% and the yield of phthalates with respect to the converted benzoate was 98.8%.

While the invention has now been described in terms of various preferred embodiments, the skilled artisan will readily appreciate that various substitutions, modifications, changes and omissions, may be made without departing from the spirit thereof. Accordingly, it is intended that the scope of the invention be limited solely by that of the following claims.

What is claimed is:

1. A process for the continuous rearrangement of an alkali metal salt of an aromatic carboxylic acid comprising continuously introducing a suspension of an alkali metal salt of an aromatic carboxylic acid in an inert organic diluent into a reaction zone via a feeding circuit comprising a feeding device including means for preheating the suspension, under an atmosphere of carbon dioxide, said carbon dioxide being introduced at a point in the feeding circuit where the temperature is lower than the temperature required to initiate the rearrangement reaction.

2. The process as defined in claim 1, wherein the carbon dioxide is introduced into the feeding circuit at a point where the temperature is between about 70° and 350° C.

3. The process as defined by claim 1, wherein the carbon dioxide is introduced into the suspension of said alkali metal salt and diluent prior to preheating.

4. The process as defined by claim 1, wherein the partial pressure of the carbon dioxide in both the feeding circuit and reaction zone exceeds about 20 bars.

5. The process as defined by claim 4, wherein the partial pressure of the carbon dioxide in both the feeding circuit and reaction zone is between about 30 and 200 bars.

6. The process as defined by claim 1, wherein said alkali metal salt of an aromatic carboxylic acid is potassium benzoate.

7. The process as defined by claim 1, wherein said inert organic diluent comprises an aromatic hydrocarbon having at least three benzene rings.

8. The process as defined by claim 7, wherein said inert organic diluent consists essentially of terphenyl compounds.

9. The process as defined by claim 8, wherein said diluent consists of o-, m-, and p-terphenyls, wherein the amount of p-terphenyl is less than about 6% of the total mass of the diluent.

10. The process as defined by claim 7, wherein said diluent consists of o-, m-, and p-terphenyls and higher polyphenyls, wherein the amount of p-terphenyl is less than about 6% and the amount of the higher polyphenyls is less than about 60% of the total mass of the diluent.

11. The process as defined by claim 1, wherein said rearrangement process is conducted in the presence of a catalyst.

12. The process as defined by claim 11, wherein said catalyst is introduced directly into the reaction zone in the form of a suspension in the inert organic diluent.

13. The process as defined by claim 11, wherein said catalyst is introduced directly into the reaction zone in the form of a solution in ther inert organic diluent.

14. The process as defined by claim 1, further comprising separating the rearranged alkali metal salt of the aromatic carboxylic acid from the reaction zone and treating it with acid to produce the aromatic carboxylic acid.

15. The process as defined by claim 6, wherein the rearranged alkali metal salt of said potassium benzoate is dipotassium terephthalate.

16. The process as defined by claim 15, wherein said dipotassium terephthalate is separated from the reaction zone and treated with hydrochloric acid to form terephthalic acid.

17. A process for the continuous rearrangement of an alkali metal salt of an aromatic carboxylic acid in the absence of a promoter comprising continuously introducing a suspension of an alkali metal salt of an aromatic carboxylic acid in an inert organic diluent into a reaction zone via a feeding circuit comprising a feeding device including means for preheating the suspension, under an atmosphere of carbon dioxide, said carbon dioxide being introduced at a point in the feeding circuit where the temperature is lower than the temperature required to initiate the rearrangement reaction.

* * * * *